United States Patent
Rolston

(10) Patent No.: US 10,107,722 B2
(45) Date of Patent: Oct. 23, 2018

(54) IN-LINE THERMAL ISOLATOR FOR LIQUID SAMPLE CONDITIONING

(71) Applicant: Mustang Sampling LLC, Ravenswood, WV (US)

(72) Inventor: Claude A. Rolston, St. Marys, WV (US)

(73) Assignee: Mustang Sampling LLC, Ravenswood, WV (US)

(*) Notice: Subject to any disclaimer, the term of this patent is extended or adjusted under 35 U.S.C. 154(b) by 173 days.

(21) Appl. No.: 15/067,689

(22) Filed: Mar. 11, 2016

(65) Prior Publication Data

US 2017/0122848 A1 May 4, 2017

Related U.S. Application Data

(60) Provisional application No. 62/248,120, filed on Oct. 29, 2015.

(51) Int. Cl.
*G01N 1/22* (2006.01)
*G01N 1/10* (2006.01)

(52) U.S. Cl.
CPC ............ *G01N 1/2202* (2013.01); *G01N 1/10* (2013.01); *G01N 1/2226* (2013.01); *G01N 2001/105* (2013.01); *G01N 2001/2238* (2013.01)

(58) Field of Classification Search
CPC G01N 1/405; G01N 1/02; G01N 1/22; G01N 2001/028; G01N 1/2205; G01N 1/2202
USPC ............... 73/863.12, 863.71, 863.16, 863.32
See application file for complete search history.

(56) References Cited

U.S. PATENT DOCUMENTS

| | | | | |
|---|---|---|---|---|
| 2,790,842 A * | 4/1957 | Nicholas | ............... | H01B 17/28 174/152 R |
| 2,952,387 A * | 9/1960 | Fowler | ................ | B67D 7/3209 137/460 |
| 3,101,863 A * | 8/1963 | Jackson, Sr. | ............ | F16K 13/04 215/233 |
| 4,034,611 A * | 7/1977 | Horling | ................ | G01N 1/2202 73/863.12 |
| 4,487,080 A | 12/1984 | Leaseburge et al. | | |
| 5,065,139 A * | 11/1991 | Shefsky | ............... | G01F 23/265 324/662 |
| 5,824,919 A * | 10/1998 | Hansen | .................... | G01N 1/22 73/863.12 |
| 6,750,730 B2 * | 6/2004 | Heisen | ...................... | H01P 1/39 333/1 |
| 7,484,404 B2 * | 2/2009 | Thompson | ................ | F17C 6/00 62/50.2 |
| D790,053 S * | 6/2017 | Querrey | ....................... | D23/393 |
| 2003/0116091 A1 | 6/2003 | Grant et al. | | |
| 2003/0233890 A1 * | 12/2003 | Mayeaux | ............. | G01N 1/2035 73/863.12 |
| 2006/0051252 A1 * | 3/2006 | Yuan | ...................... | B01L 3/0217 422/400 |
| 2008/0282814 A1 * | 11/2008 | Coleman | .............. | G01N 1/2247 73/863.71 |

(Continued)

*Primary Examiner* — Eric S McCall
*Assistant Examiner* — Mohammed E Keramet-Amircola
(74) *Attorney, Agent, or Firm* — Cahn & Samuels, LLP

(57) ABSTRACT

A generally cylindrical, elongated thermal isolator for in-line placement proximate to a vaporizer of a sample take-off conditioning system for minimizing upstream heat migration from a sample vaporizer to prevent liquid sample pre-vaporization.

5 Claims, 6 Drawing Sheets

(56) References Cited

U.S. PATENT DOCUMENTS

| | | | | |
|---|---|---|---|---|
| 2009/0151427 A1* | 6/2009 | Thompson | ............... | F17C 6/00 |
| | | | | 73/23.41 |
| 2011/0006968 A1* | 1/2011 | Morrow | ................ | H01Q 1/084 |
| | | | | 343/882 |
| 2011/0277563 A1* | 11/2011 | Scott | ................... | G01N 1/2214 |
| | | | | 73/863.12 |
| 2012/0110931 A1* | 5/2012 | Eiffert | .................... | F24J 2/5237 |
| | | | | 52/173.3 |
| 2012/0292476 A1* | 11/2012 | Smith | .................... | B64G 1/641 |
| | | | | 248/550 |
| 2012/0325694 A1* | 12/2012 | Thompson | ............ | B65D 81/38 |
| | | | | 206/216 |
| 2013/0312542 A1* | 11/2013 | Rolston | ................. | G01D 11/24 |
| | | | | 73/863.12 |
| 2014/0144254 A1* | 5/2014 | Thompson | ........... | G01N 1/2247 |
| | | | | 73/863.11 |
| 2014/0218049 A1* | 8/2014 | Sawamoto | ............ | G01N 22/04 |
| | | | | 324/640 |
| 2014/0260695 A1* | 9/2014 | Thompson | ........... | G01N 1/2035 |
| | | | | 73/863.81 |
| 2017/0082524 A1* | 3/2017 | Curtis | ..................... | G01N 1/14 |

* cited by examiner

IN-LINE THERMAL ISOLATOR FOR LIQUID SAMPLE CONDITIONING

FIELD OF THE INVENTION

This invention relates to a fabricable, in-line, thermal isolator/break that can be used in the gas sample conditioning field. The invention also contemplates control of the volume of fluid flow and provides flow restriction to the entry of an associated sample vaporizer such as the Applicant's Mustang Model 2 sample condition system and like that described and disclosed in U.S. Pat. No. 7,484,404 and its progeny, the content of which is incorporated herein by reference.

BACKGROUND

In the gas sample conditioning field, particularly when dealing with cryogenic liquids such as LNG, heat generated within a vaporizer can migrate up-stream of the vaporizer entry port and along the sample conduit tubing employed to communicate a cryogenic liquid sample from its source. (i.e., a pipeline) into the sample conditioning cabinet. Such heat energy migration has the undesirable effect of causing sample pre-vaporization before introduction of the extracted liquid sample into the vaporizer. Pre-vaporization of an incoming sample adversely impacts the accuracy of a sample analysis thereof by, for example, creating phase and fluid component partitioning within the sample, interfering with uniform sample flow into the vaporizer, and/or generating sufficient back-pressure to create a deadheading effect within the system. In the event any of the foregoing occur, the accuracy of any analysis, i.e., quantifying the energy content of a particular LNG sample, becomes suspect.

SUMMARY OF THE INVENTION

It is an object of the present invention to provide an adjunct to minimize heat migration from a sample vaporizer to a liquid sample conduit.

It is another object of the present invention to also enhance sample fluid flow control by reducing a sample volume passing through the adjunct.

These and other objects are satisfied by an embodiment of the invention characterized by an in-line thermal isolator disposed proximate to the entry port of a sample vaporizer to minimize heat migration from a sample vaporizer to the upstream sample conduit, the isolator featuring an elongated, generally cylindrical body incorporating an axial bore for accommodating fluid flow from a sample source, and a fitting member adapted for in-line sealable connection with a mating member formed in the sample conduit.

The invention provides a second embodiment to the first embodiment further characterized by the in-line thermal isolator formed from a polymeric material selected from the group consisting of PETE and PEEK.

The invention provides a third embodiment to the previous embodiments further characterized by the axial bore where the in-line thermal isolator restricts fluid flow.

The invention provides a further embodiment to the previous embodiment further characterized by the in-line thermal isolator with compression fittings on each end.

The invention provides a further embodiment to the first embodiment further characterized by the in-line thermal isolator formed from a thermally insulative material being selected from the group consisting of synthetic polymers and ceramics.

A further embodiment of the invention is characterized by a method of preventing thermally-induced sample pre-vaporization in a sample conduit comprising the step of inserting an isolator according to any of the previous embodiments upstream from a sample vaporizer in the sample conduit line to prevent heat migration.

An essential function of the invention is to provide a thermal break/discontinuity in sample tubing conveying, for example, cryogenic Liquid Natural Gas or non-cryogenic Natural Gas Liquids to a sample vaporizer. When connected to a LNG or NGL Vaporizer, in-line placement of the inventive thermal break prevents heat from migrating from the sample vaporizer along the tubing to thereby pre-warm an incoming liquid sample. This pre-warming prior to vaporization can cause component/phase separation of the liquid sample leading to erroneous analyzer results. In the simplest of terms, use of the invention thermally isolates two co-linear segments of metal tubing in a process sample line.

The thermal break of the invention can assume different configurations and be formed of any number of thermally-insulating, engineered materials. Functionally, a thermal break in accordance with the invention must possess a functionality of sealingly securing a liquid communication conduit while providing thermal isolation by interrupting heat transfer along tubing/conduit. Preferably, the in-line thermal isolator/break is positioned close to the sample entry port to a sample vaporizer, particularly in the case of a cryogenic liquid sample to avoid issues resulting from pre-vaporization and deadheading.

In this detailed description, references to "one embodiment", "an embodiment", or "in embodiments" mean that the feature being referred to is included in at least one embodiment of the invention. Moreover, separate references to "one embodiment", "an embodiment", or "embodiments" neither necessarily refer to the same embodiment nor does this mean such embodiments are mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, "analyte sample" contemplates a constituent from a source such as natural gas, a liquid natural gas, natural gas liquid, or a cryogenic liquid capable of vaporization and sample content characterization by conventional analysis equipment such as a gas chromatograph, mass spectrograph, Raman spectrophotometer, tunable diode laser spectrograph, etc.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

For definitional purposes and as used herein "connected" includes physical, whether direct or indirect, affixed or adjustably mounted. Thus, unless specified, "connected" is intended to embrace any operationally functional connection.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of a specific exemplary embodiment in which the invention may be practiced. The following illustrated embodiment is described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION

Figure 1:
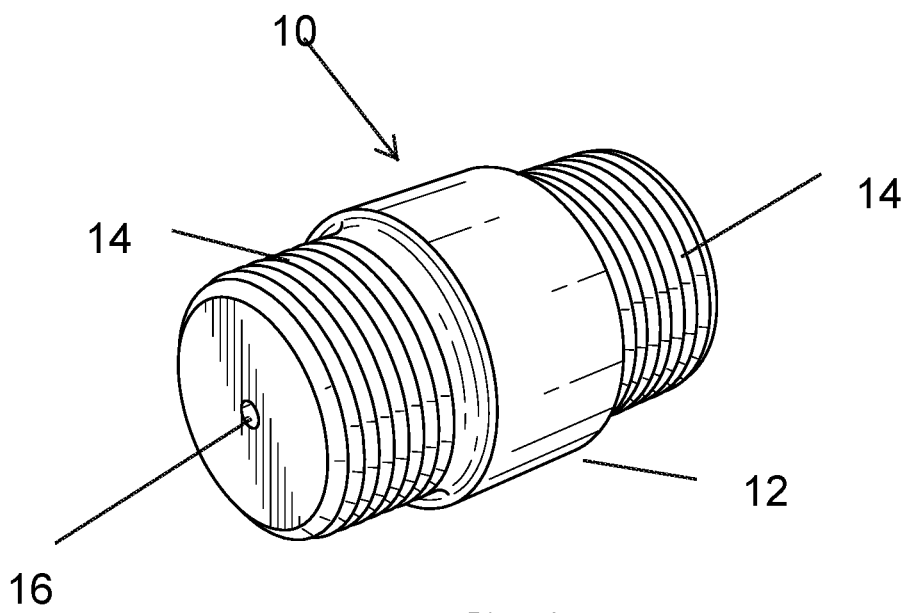
FIG. 1 is a side perspective end view of a first embodiment of the invention.
Figure 2:
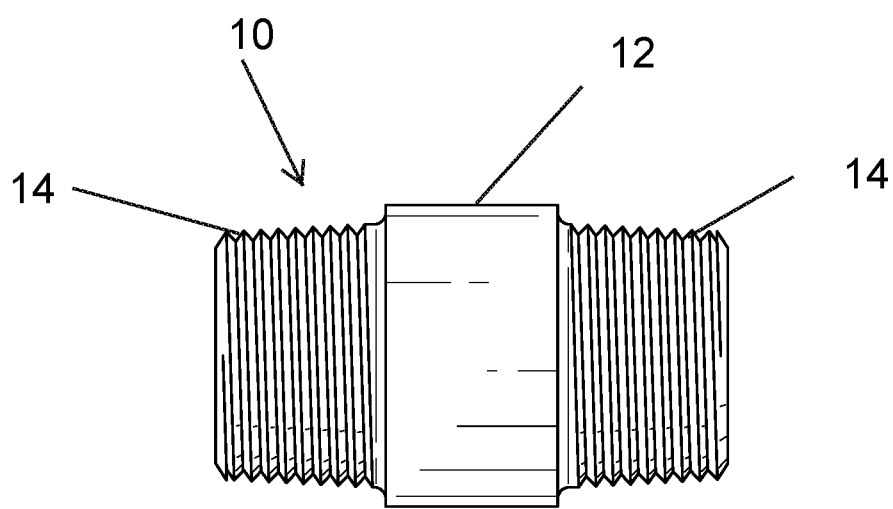
FIG. 2 is a side view of the embodiment of FIG. 1.
Figure 3:
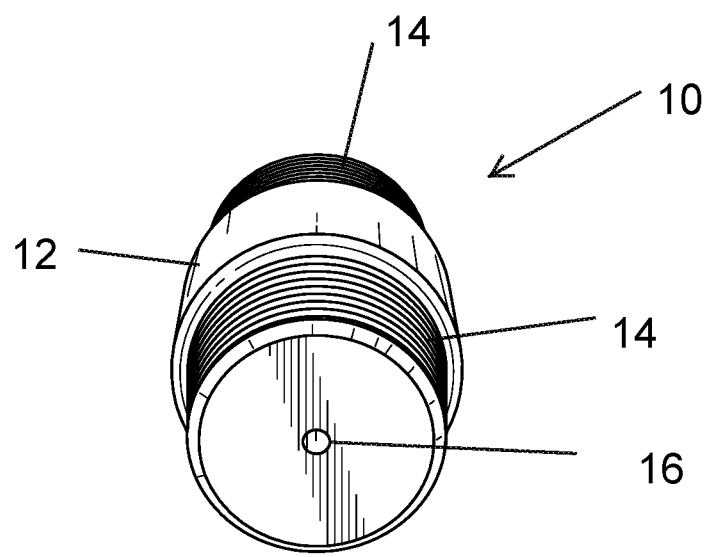
FIG. 3 is a perspective end view of the embodiment of FIG. 1.
Figure 4:
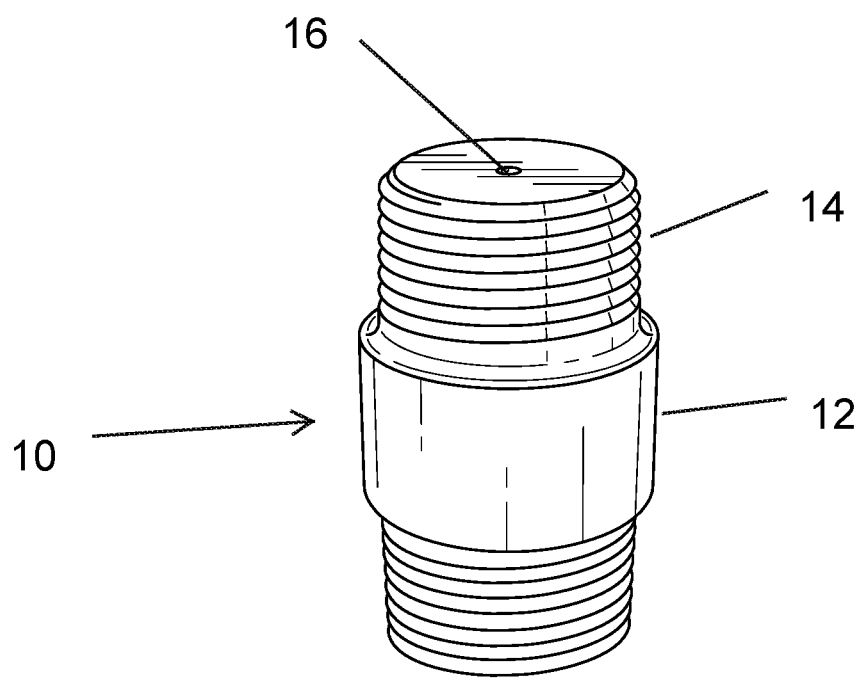
FIG. 4 is a further side view of the embodiment of FIG. 1.

FIGS. 1-6 depict a Process Thermal Isolator structure 10 contemplated by the invention. The isolator 10 refines a relatively cylindrical body defined by a central annular section 12 and threaded connectors 14. The threaded connectors 14 project oppositely of the annular section 12 and feature an axially-oriented, fluid passage, bore 16.

The material selected for fabrication of the isolator 10 must demonstrate sufficient resistance to burst at very high pressures and to thermal stresses even at cryogenic temperatures. Preferably, the composition of the thermal isolator/break is a highly-engineered, burst-resistant, thermally-stable composition, preferably formed from a polymeric material such as PETE (polyethylene terephthalate) or PEEK particularly suited for disposition between a sample takeoff manifold and vacuum jacketed tubing to prevent migration of frost to the vaporizer and heat to the upstream tubing of the vaporizer. Alternative materials can be employed, e.g., other synthetic polymers, ceramics, etc., so long as they possess the necessary degree of thermal stability and burst resistance while providing the ability for precision molding/machining into the desired engineered configuration.

Figure 5:
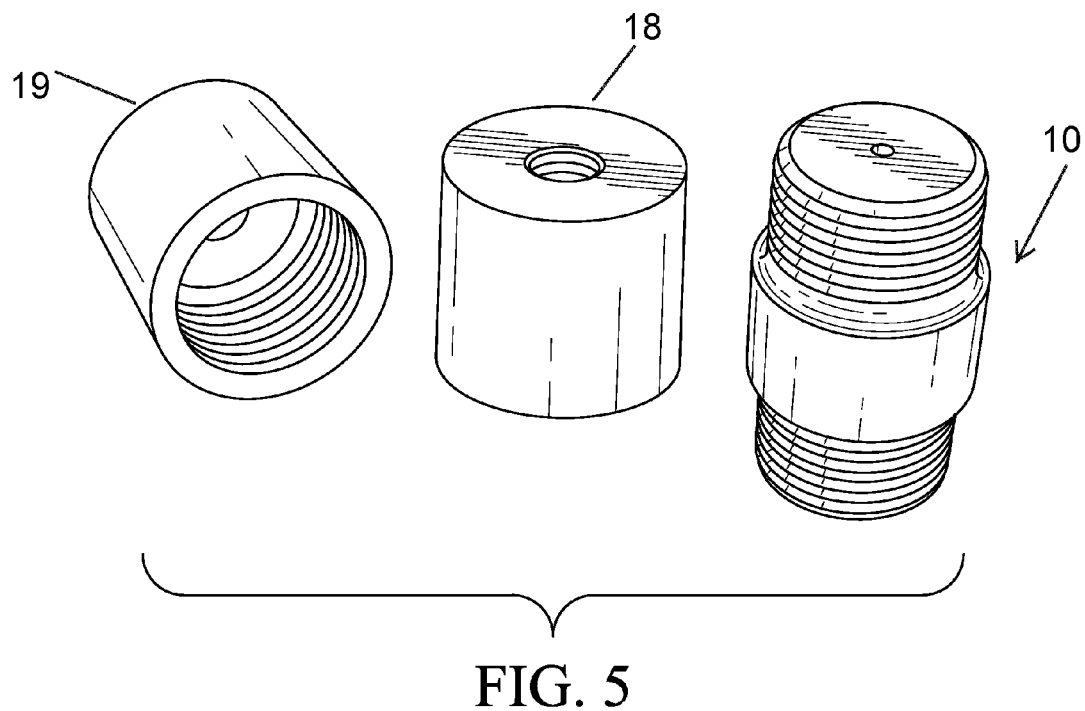
FIG. 5 is an exploded view of the embodiment of FIG. 1 with threaded metal end caps for connecting to the sample line (not illustrated).
Figure 6:
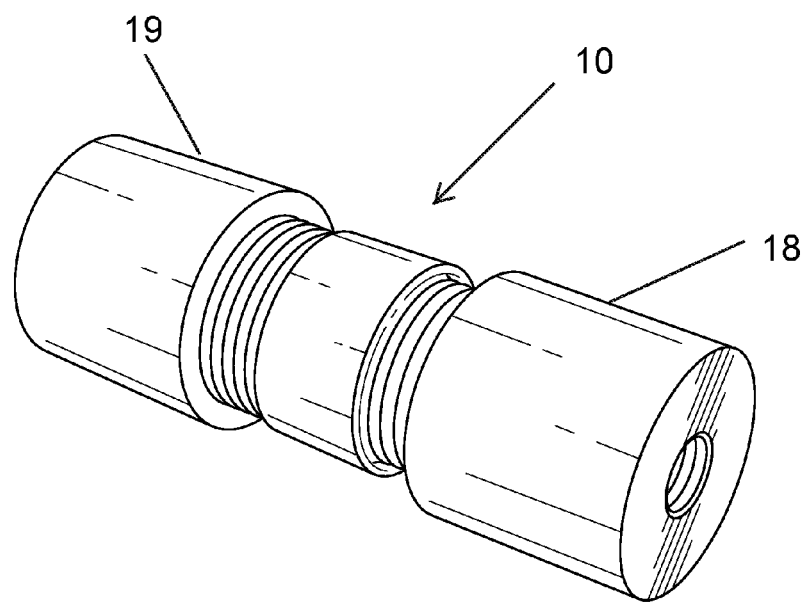
FIG. 6 is a perspective side assembly view of the components depicted in FIG. 5.

Referring to FIGS. 5 and 6, each respectively illustrates in assembly and assembled view, thermal isolator 10 and female threaded compression end caps 18, 20 for securing the thermal isolator 10 in a liquid sample line.

Figure 7:
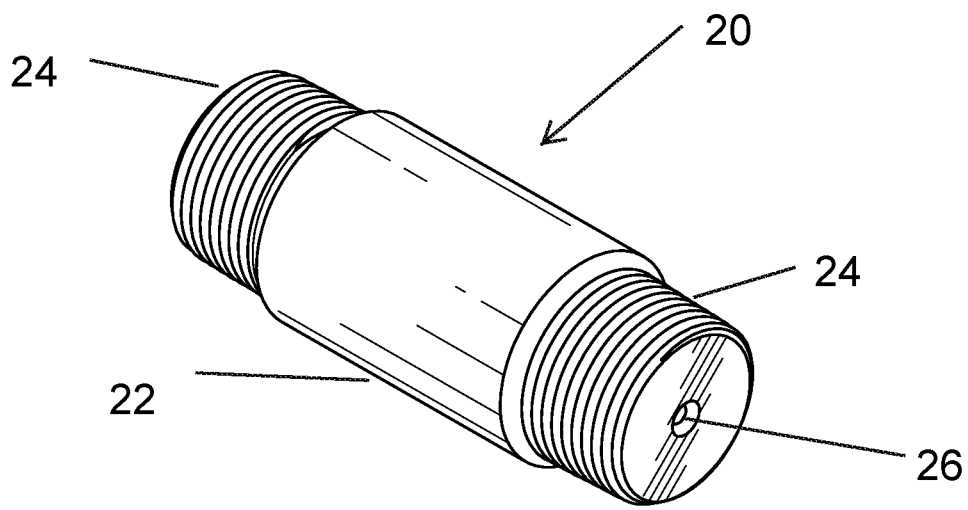
FIG. 7 is a view of an elongated alternative embodiment in accordance with the invention.
Figure 8:
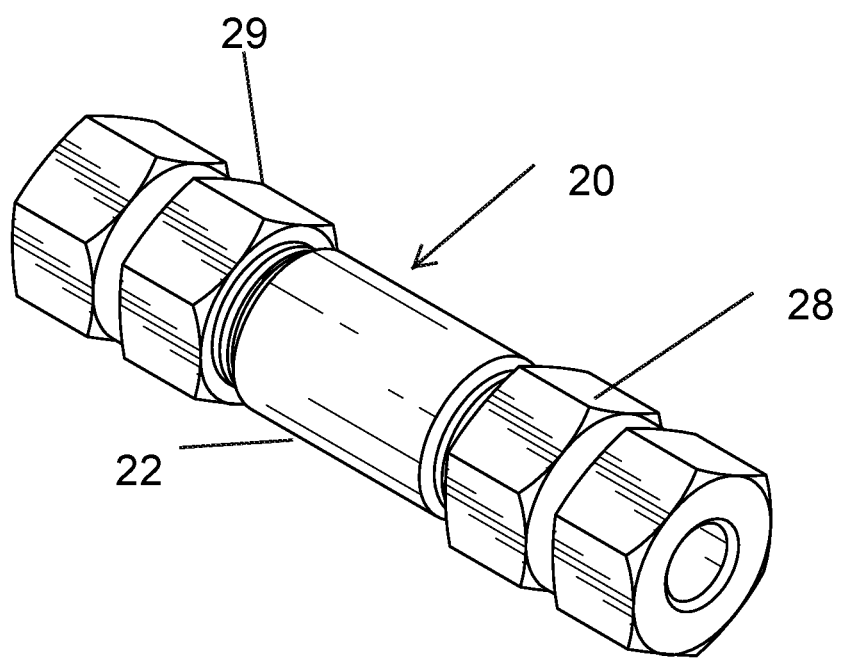
FIG. 8 is a perspective side assembly view of the embodiment of FIG. 7 with in-line, nut style compression fitting connectors.

Illustrated in FIGS. 7-8 is an elongated version of a thermal isolator 20, where the annular segment 22 is of greater length than its shorter counterpart 12 illustrated in FIGS. 1-6. The remaining structures, threaded connectors 24, and the central bore 26 are substantially structurally identical to their respective counterparts 14, 16 illustrated in FIGS. 1-6. The end fittings of FIG. 8 are unthreaded compression fittings 28, 29 that sealingly secure the isolator 20 in-line with an associated liquid sample pipeline (not illustrated).

Figure 9:
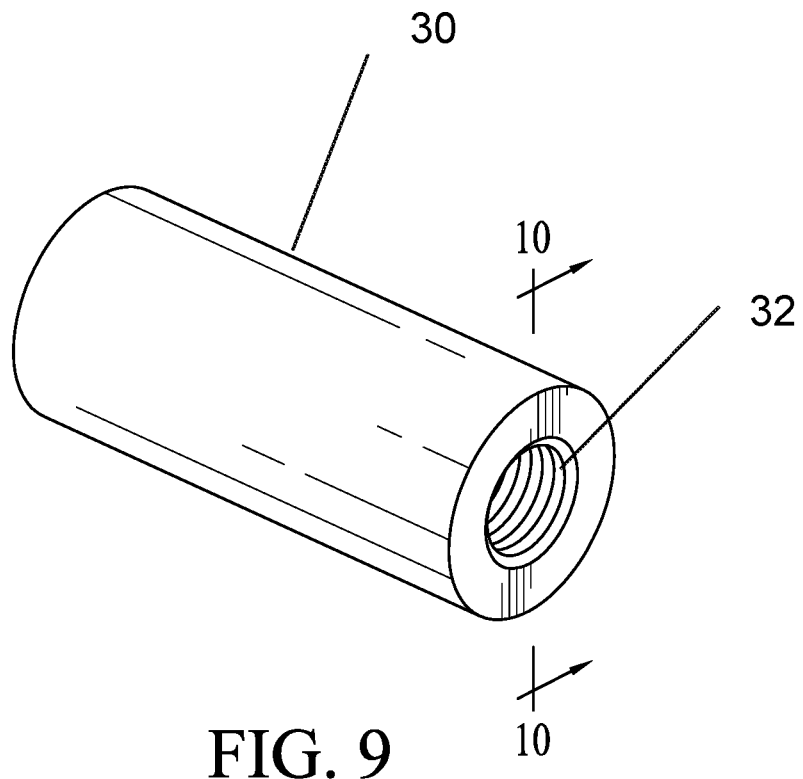
FIG. 9 is a perspective view of a further alternative embodiment of the invention providing a smooth, outer cylindrical surface in accordance with the invention.
Figure 10:
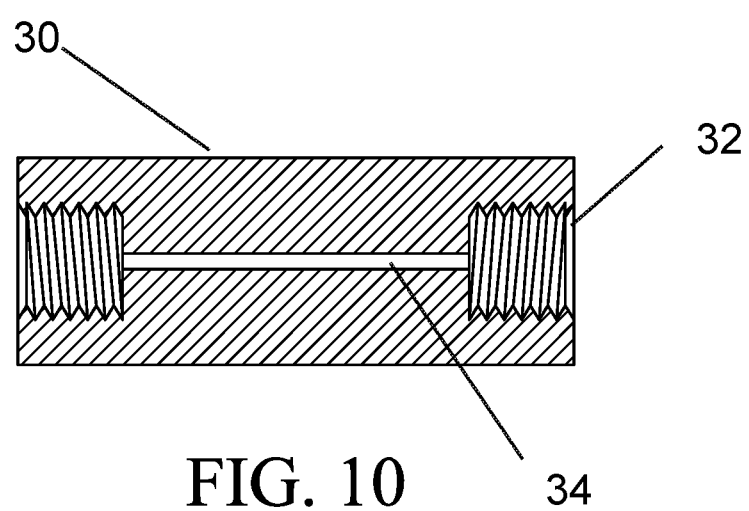
FIG. 10 is a cutaway side view of the embodiment of FIG. 9 illustrating the unitary elongated body with in-line threading for sealingly receiving a correspondingly-sized, threaded, tubing connector.

The variation of the invention illustrated in FIGS. 9 and 10 provides an isolator 30 with a smooth continuous cylindrical outer surface that includes female-threaded, axial openings 32 for securing corresponding threaded male members formed on the associated liquid sample line. The isolator 30 includes an axial bore 34 of reduced diameter for flow control. It is a matter of design choice whether the isolator is a screw on or screw in version.

Figure 11:
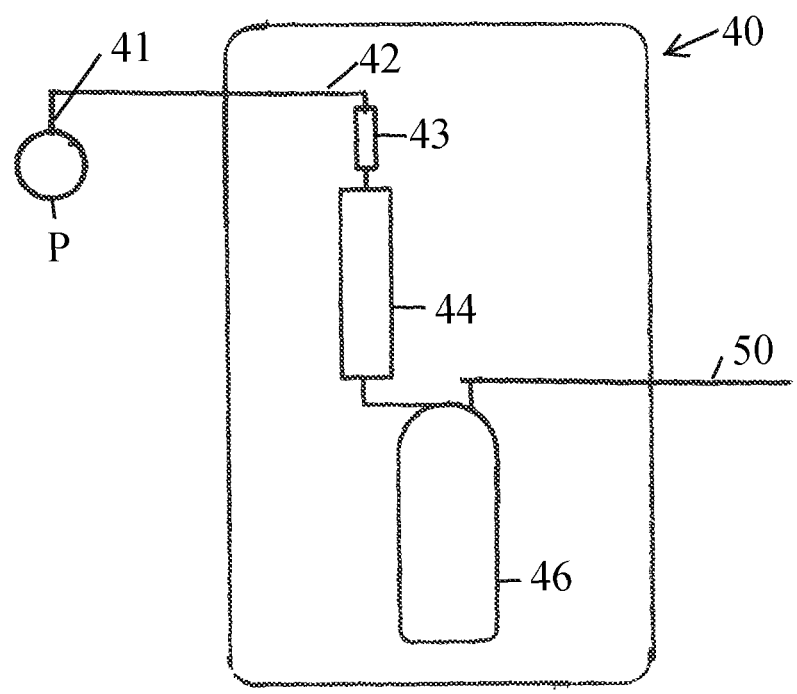
FIG. 11 is a simplified schematic representation of a thermal isolator in relation to a sample vaporizer system according to the invention.

FIG. 11 illustrates exemplary in-line placement of a thermal isolator 42 according to the invention. The illustrated generic arrangement includes a heated enclosure 40 of the type described in any one of Applicant's earlier issued patents, U.S. Pat. No. 7,162,933, U.S. Pat. No. 7,484,404, or U.S. Pat. No. 9,057,668, all being incorporated herein by reference. The enclosure 40 is positioned near a pipeline P and includes a takeoff probe 41 and an analyte sample takeoff line 42 with a thermal isolator 43 disposed in-line proximate to an analyte sample vaporizer unit 44. The vaporizer unit 44 is associated with flow control valves as well as heat and pressure regulators (not illustrated) and vaporized gas input to a mixing accumulator 46 for throughput without dew point drop out caused by Joules-Thompson condensation or the like, to a thermally insulated analyzer output line 50 exiting the heated enclosure 40.

It should be understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the description invention.

I claim:

1. A fluid sample vaporization system, comprising:
a fluid sample vaporizer, said sample vaporizer having an entry port defining a first thermal zone;

a sample input conduit defining a second thermal zone, said sample conduit being located upstream of said sample vaporizer; and an in-line thermal isolator, said in-line thermal isolator defining a body of a select length and having a first end and a second end, said body including an axial bore therethrough extending from first end to second end; said first end being sealingly engaged with said sample input conduit and said second end being sealingly engaged with said entry port to prevent heat energy transfer between said first and second thermal zones.

2. The fluid sample vaporization system of claim 1 where the in-line thermal isolator is formed from a polymeric material selected from the group consisting of PETE and PEEK.

3. The fluid sample vaporization system of claim 1 where the axial bore restricts fluid flow.

4. The fluid sample vaporization system of claim 1 further comprising compression fittings on each of said first and second ends.

5. The fluid sample vaporization system of claim 1 where the thermal isolator body defines a cylindrical structure where each of said first and second ends features male threading.

* * * * *